(12) United States Patent
Kim

(10) Patent No.: US 7,816,962 B2
(45) Date of Patent: *Oct. 19, 2010

(54) DELAY LOCKED LOOP WITH IMPROVED JITTER AND CLOCK DELAY COMPENSATING METHOD THEREOF

(75) Inventor: Kyung-Hoon Kim, Ichon-shi (KR)

(73) Assignee: Hynix Semiconductor Inc., Kyoungki-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 12/284,060

(22) Filed: Sep. 18, 2008

(65) Prior Publication Data

US 2009/0033392 A1    Feb. 5, 2009

Related U.S. Application Data

(63) Continuation of application No. 10/746,226, filed on Dec. 23, 2003, now Pat. No. 7,436,230.

(30) Foreign Application Priority Data

Jul. 29, 2003    (KR) ................ 2003-52288

(51) Int. Cl.
H03L 7/06    (2006.01)
(52) U.S. Cl. ...................... 327/158; 327/149
(58) Field of Classification Search ............ 327/149, 327/158
See application file for complete search history.

(56) References Cited

U.S. PATENT DOCUMENTS

| 5,614,855 | A | 3/1997 | Lee et al. | |
|---|---|---|---|---|
| 5,815,016 | A | 9/1998 | Erickson | |
| 5,977,801 | A | 11/1999 | Boerstler | |
| 6,037,812 | A | 3/2000 | Gaudet | |
| 6,240,152 | B1 | 5/2001 | Ho | |
| 6,242,954 | B1 | 6/2001 | Taniguchi et al. | |
| 6,433,597 | B2 * | 8/2002 | Jung | 327/158 |
| 6,434,540 | B1 | 8/2002 | Numaoka | |
| 6,483,886 | B1 | 11/2002 | Sung et al. | |
| 6,593,786 | B2 * | 7/2003 | Jung | 327/158 |
| 6,822,494 | B2 * | 11/2004 | Kim | 327/160 |
| 7,098,712 | B2 * | 8/2006 | Lee | 327/161 |
| 2002/0000856 | A1 * | 1/2002 | Jung | 327/158 |
| 2002/0057119 | A1 | 5/2002 | Stubbs et al. | |

(Continued)

FOREIGN PATENT DOCUMENTS

JP    60-224345    11/1985

(Continued)

*Primary Examiner*—Lincoln Donovan
*Assistant Examiner*—William Hernandez
(74) *Attorney, Agent, or Firm*—Blakely, Sokoloff, Taylor & Zafman LLP

(57) ABSTRACT

A delay locked loop can remove a jitter component that inevitably occurs due to feedback latency in the conventional DLL. That is, the present invention has benefit of removing the jitter component by controlling the delay lines based on the predicted data. The delay locked loop includes a pattern detecting unit for generating and storing a noise pattern by detecting inputted noise data, a pre-delay control unit for determining a delay amount depending on the output of the pattern detecting unit, and a pre-delay line for delaying an internal clock depending on the delay amount that is determined by the pre-delay control means.

10 Claims, 18 Drawing Sheets

U.S. PATENT DOCUMENTS

2002/0196062 A1   12/2002   Iwashita

FOREIGN PATENT DOCUMENTS

| | | |
|---|---|---|
| JP | 11-316618 | 11/1999 |
| JP | 2002 049438 | 2/2002 |
| KR | 1020020002565 | 1/2002 |
| TW | 502502 | 9/2002 |

* cited by examiner

DELAY LOCKED LOOP WITH IMPROVED JITTER AND CLOCK DELAY COMPENSATING METHOD THEREOF

The present patent application is a Continuation of application Ser. No. 10/746,226, filed Dec. 23, 2003 now U.S. Pat. No. 7,436,230.

FIELD OF THE INVENTION

The present invention relates to a DLL (Delay Locked Loop) having an improved jitter characteristic; and, more particularly, to a DLL capable of reducing a jitter by estimating and compensating a delay difference before phase comparison in a conventional DLL, based on a noise pattern that is detected by monitoring Vdd power noise.

BACKGROUND OF THE INVENTION

Generally, a clock in a system or a circuit is used as a reference for operation timing, or used to guarantee fast operation without error. When an external inputted clock is used inside the system or the circuit, time delay (or, clock skew) happens due to the internal circuit. Therefore, a DLL (Delay Locked Loop) is introduced to compensate such a time delay so that an internal clock can have same phase as the external clock. That is, the DLL fits output timing of data, that is sensed by using the external clock and outputted through an output buffer, to the timing of the external clock.

It will be described for an example where the DLL is applied in a DDR SDRAM in the prior art.

FIG. 1 provides a block diagram of a register controlled DLL of a DDR SDRAM in the prior art.

The register controlled DLL of the DDR SDRAM in the prior art comprises a clock buffer unit 11, a clock divider unit 12, a dummy delay line unit 13, a delay modeling unit 14, a phase comparator unit 15, a delay controlling unit 16 and a delay line unit 17. The clock buffer unit 11 receives an external clock signal clk, clkb to its input to generate internal clocks rclk, fclk that are synchronized to the rising edge and the falling edge of the external clock signal clk, clkb. The clock divider unit 12 divides the external clock clk to 1/n (n being a positive integer) to output a reference clock ref. The dummy delay line unit 13 receives the reference clock ref as its input. The delay modeling unit 14 receives the output clock fbk_dly from the dummy delay line unit 13 to make it go through the same condition as the actual clock path. The phase comparator unit 15 compares the phase of the output fbk of the delay modeling unit 14 to that of the reference clock ref to output a shift control signal. The delay controlling unit 16 outputs a signal for shifting the clock phases of the delay line and the dummy delay line in response to the shift control signal from the phase comparator unit 15. The delay line unit 17 shifts the internal clocks rclk, fclk based on the output signal from the delay controlling unit 16.

It will be described for each part of the DLL in detail.

FIG. 2 is a detailed circuit diagram of the clock buffer unit 11 in the prior art.

The clock buffer unit 11 as shown in FIG. 2 receives the external clock clk, clkb to a differential comparing circuit to generate the internal clock rclk that is synchronized to the rising edge of the external clock. There is included a separate clock buffer for the dummy delay line unit that will be well understood by the skilled person in the art. Therefore, its detailed description will be omitted for sake of simplicity.

FIG. 3 describes a detailed circuit diagram of the clock divider unit 12 in the prior art.

The clock divider unit 12 as shown in FIG. 3 divides the frequency of the external clock to ⅛. Here, the reason why the external clock is divided is for reducing power consumption. The operations of the clock divider circuit will be well understood by the skilled person in the art. Therefore, its detailed description will be omitted for sake of simplicity.

FIG. 4 shows a detailed circuit diagram of the phase comparator unit 15 in the prior art.

The phase comparator 15 compares the phase of the input clock to that of the output clock to detect the phase difference between the two clocks. The phase comparator unit 15 compares the phase of the reference clock from the clock divider unit 12 to that of the feedback clock fbk from the delay modeling unit 14. Based on the comparison result, one of lead, lag and locking information is outputted to the delay controlling unit 16. Referring to FIG. 4, shifting right is performed depending on the comparison signals PC1, PC3 and shifting left is performed depending on the comparison signals PC2, PC4. Further, it is determined whether the shift operation is performed by using the un-divided clock rclk or by using the divided reference clock based on comparison between the reference clock ref and the feedback clock fbk. That is, if the phase difference between the reference clock ref and the feedback clock fbk is greater than the delay time of a long delay cell, the comparison signal PC5 or the signal PC6 becomes 'H' state. In turn, AC that is logic sum of the signal PC5 and the signal PC6 becomes the 'H' state and is logically combined with the un-divided clock rclk to come out of the phase comparator 151 to operate a shift register control signal generator 152 and a T-F/F (flipflop). In other words, when the phase difference between the reference clock ref and the feedback clock fbk is great, that phase difference is to be reduced fast by operating the shift register with the un-divided clock. Upon reducing the phase difference to a predetermined level, the two signals PC5, PC6 are made to go to the 'H' state to operate the shift register with the divided clock.

FIG. 5 represents a detailed circuit diagram of the delay control unit 16 in the prior art.

The delay control unit 16 is constructed by one part for determining the input path of the clock in the delay line unit and the other part including a bi-directional shift register for changing the path position. The shift register in the delay controlling unit 16 performs the shift operation by using 4 input signals and has a maximum or minimum delay by making its initial input condition such that its most right signal or most left signal is in the 'H' state. The input signals to the shift register are a shift right even signal, a shift right odd signal, a shift left even signal and a shift left odd signal. For shift operation, two of the signals in the 'H' state should not be overlapped.

FIG. 6 illustrates a detailed circuit diagram of the delay line unit 17 in the prior art.

The delay line unit 17 is a circuit for delaying the phase of the external clock. Here, the amount of the delay is determined by the phase comparator 15, and the delay line unit 17 forms a delay path that determines the phase delay under control of the delay controlling unit 16. The delay line unit 17 includes a number of unit delay cells that are serially coupled to each other. The unit delay cell includes 2 NAND gates that are serially coupled to each other. The input of each of the unit delay cells is connected to the shift register in the delay controlling unit 16 in one-to-one mapping, where only one of the shift registers outputs the 'H' state to have the path for the reference clock. The delay line unit 17 is constructed with 2 delay lines of one delay line for the rising clock and the other delay line for the falling clock in the DDR SDRAM to suppress duty ratio distortion as much as possible by identically processing the rising edge and the falling edge.

Through a particular circuit is not shown, the dummy delay line unit 13 is a delay line for feedback clock that is inputted to the phase comparator unit 15 and its constitution is similar to that of the delay line unit 17 in FIG. 6 except that the divided clock is inputted to the dummy delay line unit 13 so that power consumption can be reduced. The delay modeling unit 14 models the front part of the delay line unit 17 from the input of the external clock to a chip, and delay factors that the output clock of the delay line unit 17 goes through till the output clock exits the chip. The clock signal line is a path that the clock goes through from the delay line unit 17 to an output buffer. The output buffer synchronizes data to the clock on the clock signal line to output the data through an external output port.

The DLL as described above continuously compares the external clock to the internal clock to synchronize the two clocks, and detects information about the phase difference between the two clocks to adjust the delay lines to reduce the phase difference. However, if noise is not considered in the DLL, there should exist a phase error due to the resolution of the unit delay cell, i.e., a skew, to make locked only with the phase error of the resolution of the unit delay cell. Once the noise is considered, a jitter due to the noise should be considered in addition to the skew.

The jitter occurs due to thermal noise and flicker noise in addition to external or internal power noise. Due to the jitter, in the phase comparator of the DLL, locking point varies with continuous comparison of the two clocks. Though that variation of the locking point could compensate the external or internal noise, but cannot compensate the difference between the comparison time of the phase comparator and the generation time of the actual noise. In this reason, a phase margin is introduced to a PLL (Phase Locked Loop) or the DLL.

FIG. 7 shows a diagram for exemplifying case by case a reaction time and applying time of the noise that occurs in the DDL circuit in the prior art.

The noise occurs before the delay lines and at the phase comparator and replica model.

First, it will be described for the delay due to the noise that occurs before the delay lines (Hereinafter, it will be called as a first delay factor). The first delay factor is generated due to the power noise of the delay lines, the thermal noise of transistors and the flicker noise.

Assuming that the point when the amount of the delay starts to vary due to the noise is 0, the clock is inputted to the replica model 14 at a delayed timing 'Tclk−td2' (For locking of the DLL, Tclk is the clock period and td2 is the delay time of replica) after passing the dummy delay line 13. Then, the clock is inputted to the phase comparator at 'Tclk' delayed timing after passing the replica model 14. That is, after 'Tclk', delay compensation is performed at the phase comparator unit 15. Because the result of the phase comparator unit 15 should have more delay with passing the register controller and the shift register in the delay controller 16, the actual timing when the delay compensation is applied to the delay lines is at least after 2Tclk when there is no low-pass-filter used, but the actual timing will be even more delayed when there is any low-pass-filter used. In other words, due to the first delay factor, there will be a delay of 2Tclk through the dummy delay line 13, the replica model 14 and the delay controller 15.

Next, it will be described for the delay due to the noise that occurs at the replica model (Hereinafter, it will be called as a second delay factor). The reason for occurrence of the second delay factor is similar to that of the first delay factor.

If the replica model 14 is equal to noise environment, the delay at the replica model 14 should be varied depending on the noise occurrence timing. However, assuming that the noise occurrence timing at the replica model 14 is 0, the clock is inputted to the phase comparator 15 at a 'td2' delayed timing after passing the replica model 14 and the delayed clock from the phase comparator 15 is delayed again passing the register controller and the shift register in the delay controller 16. Therefore, because the delay time in the delay controller 16 is greater than Tclk, the actual timing when the delay compensation is applied to the delay line 17 is after 'Tclk+td2', but the actual timing will be even more delayed when there is any low-pass-filter used. In other words, due to the second delay factor, there will be 'Tclk+td2' delay through the replica model 14 and the delay controller 15.

Finally, it will be described for the delay due to the noise at the phase comparator unit 15 (Hereinafter, it will be called as a third delay factor).

Though the phase comparator unit 15 is robust to the noise compared to other circuits, it would be affected by the noise due to mismatch between the paths of the feedback clock fbk and the reference clock ref on the layout and uncertainty window. Because that noise goes through the register controller and the shift register of the delay controller 16, the dummy delay line 13, the replica model 14 and the delay controller 16, it results in '3Tclk' the greatest response time.

On the other hand, the way to compensating the delay due to the noise to the DLL is blocking the noise or reducing the response time of the DLL. Here, the response time reducing method is for reducing the time before the delay lines is varied based on the information from the phase comparator. However, such a reducing method has a limitation because there always exists a delay time occurring at the other delay line and the replica model even though the response time is 0. Actually, for the low-pass-filter, opposite noise occurs when the delay line has been varied with the result from the phase comparator due to the noise and, in turn, due to that opposite noise, the delay line is to be varied in the opposite direction against the typical direction so as to generate a jitter that is 2 times greater than typical. That is, when the jitter due to the typical noise is 't_jitter', the delay line compensates that 't-jitter' but, if additional noise '−t_jitter' occurs at that time, there happens very serious noise of '−2t_jitter'.

SUMMARY OF THE INVENTION

It is, therefore, a primary object of the present invention to provide a delay locked loop capable of detecting and storing a noise pattern.

It is another object of the present invention to provide a delay locked loop capable of having various delays depending on a noise pattern.

In accordance with the present invention, there is provided a delay locked loop having a phase comparator for comparing a phase of a reference clock signal with a phase of a feedback clock signal, including a pitch out unit for storing a noise pattern that is detected by monitoring inputted noise data.

Further, the pitch out unit of the present invention includes a unit for compensating a phase delay due to newly inputted noise based on the noise pattern.

Further, the delay locked loop of the present invention, having a phase comparator for comparing a phase of a reference clock signal with a phase of a feedback clock signal, comprising a pattern detecting unit for generating and storing a noise pattern by detecting inputted noise data, a pre-delay control unit for determining a delay amount depending on the output of the pattern detecting unit, and a pre-delay line for delaying an internal clock depending on the delay amount that is determined by the pre-delay control unit.

Further, the pattern detecting unit of the present invention includes a unit for collecting the inputted noise data, a unit for generating the noise pattern based on the noise data that is collected by the gathering unit, and a unit for loading the noise pattern as same as the newly inputted noise data.

Further, the pattern detecting unit of the present invention includes a storage block for storing the inputted noise data and the noise pattern, a storage cell manager for reading or writing the stored noise data and the stored noise pattern under control of a state machine, a shift register and writer for performing shift operation by using the result of the phase comparator and up-loading data, and a pattern generator for generating the noise pattern based on the noise data.

Further, the storage block of the present invention includes a first storage block for storing the output of the phase comparator, and a second storage block for storing the output of the pattern generator.

Further, the storage cell manager of the present invention includes a first storage manager for writing inputted data or reading the stored data by selecting a desired storage cell block in the first storage block, and a second storage manager for writing inputted data or reading the stored data by selecting a desired storage cell block in the second storage block.

Further, the second storage cell manager of the present invention includes a first decoder for selecting one of a plurality of storage cell blocks in the second storing clock, and a second decoder for selecting one of a plurality of addresses in the storage cell block.

Further, the second storage cell manager of the present invention includes a counter for assigning data storing order in the storage cell block.

Further, the storage cell block of the present invention stores data for same command and same access bank.

Further, the pattern generator of the present invention includes a plurality of adders for adding the inputted data, a plurality of subtracters for subtracting the output of the adders, a plurality of threshold detectors for performing threshold operation for the outputs of the subtracters, and a plurality of data latches for temporally storing the noise pattern that is outputted from the threshold detector.

Further, the state machine of the present invention controls to classify data by the command and by the accessed bank by using a command, a bank address and a clock that are externally inputted and to store in the second storage block, and controls to read the data that is stored at the first storage block by classifying the data by the command and by the accessed bank.

Further, a clock delay compensating method of the present invention for use in a delay locked loop having a phase comparator for comparing a phase of a reference clock signal with a phase of a feedback clock signal, comprises the steps of (a) detecting a noise pattern by monitoring inputted noise data, (b) storing the detected noise pattern, and (c) compensating a phase delay due to newly inputted noise based on the noise pattern.

Further, a clock delay compensating method of the present invention for use in a delay locked loop having a phase comparator for comparing a phase of a reference clock signal with a phase of a feedback clock signal, comprises the steps of (a) receiving inputted noise data to detect and store a noise pattern, (b) determining a delay amount depending on the noise pattern, and (c) delaying an internal clock depending on the delay amount that is determined at the step (b).

Further, the step (a) of the present invention for receiving inputted noise data to detect and store a noise pattern, includes the steps of (d) collecting the noise data that is outputted from the phase comparator, (e) generating the noise pattern based on the noise data that are collected at the step (d), and (f) loading the noise pattern as same as newly inputted noise data.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

Generally, noise is white noise that has a uniform distribution over all the frequency range. However, the inventor of the present invention discovered the fact that the major noise that occurs at the DRAM has a greater value over a particular frequency range from various experiments and experiences. Particularly, the inventor of the present invention discovered and focused on the fact that the noise pattern is repetitive because of the area limitation for power lines.

The present invention has been started from that fact so that noise pattern is detected and stored. Also, while the noise corresponding to the stored pattern is inputted, delay lines of the DLL may be varied based on the stored pattern. In this procedure, the response time of the DLL becomes 0 to vary the amount of the delay accurately at ac accurate timing.

Hereinafter, with reference to the accompanying drawings, a preferred embodiment of the present invention will be explained in detail.

Figure 1:
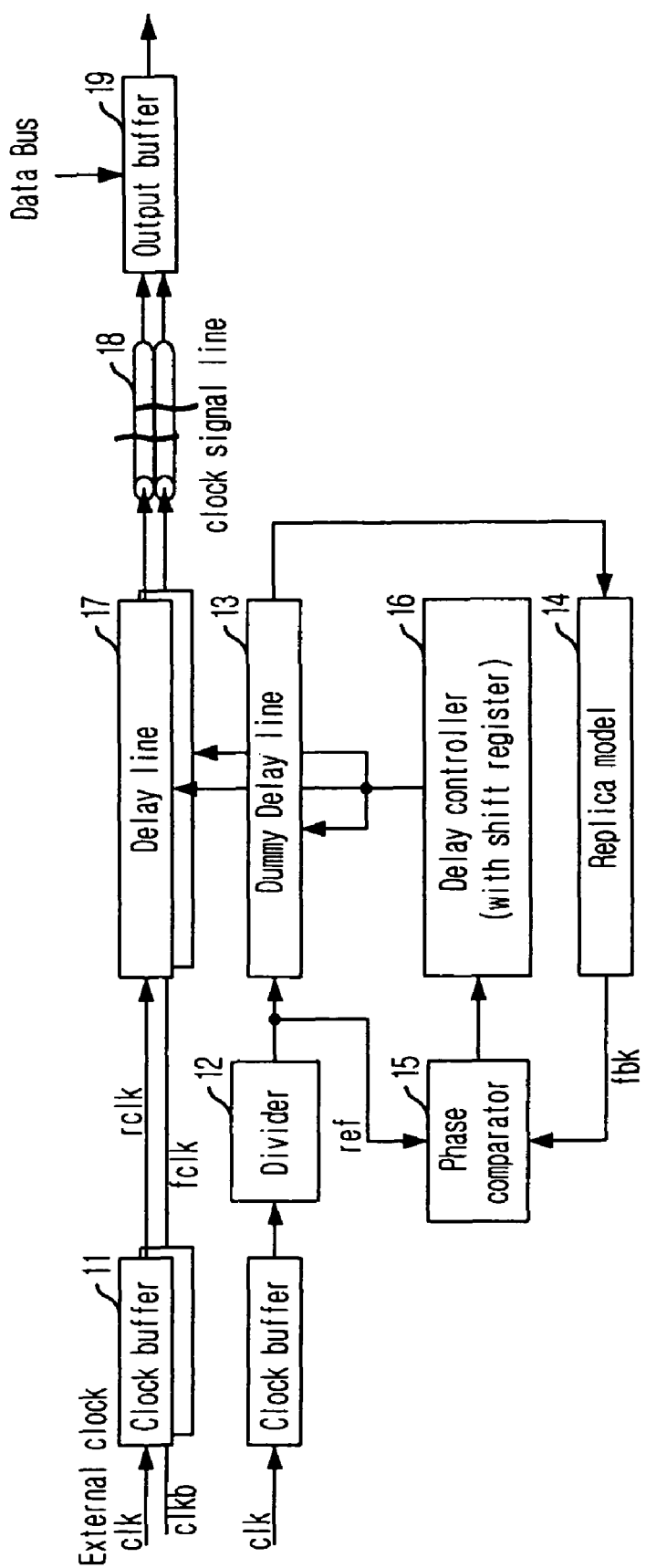
FIG. 1 provides a block diagram of a register controlled DLL of a DDR SDRAM in the prior art.
Figure 2:
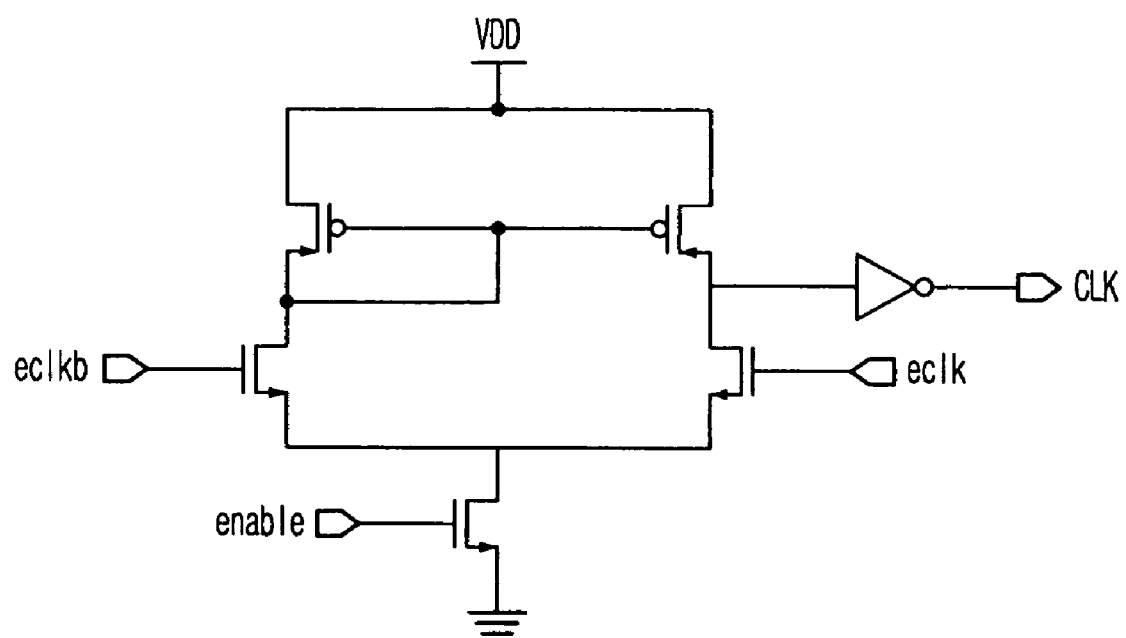
FIG. 2 is a detailed circuit diagram of a clock buffer unit in the prior art.
Figure 3:
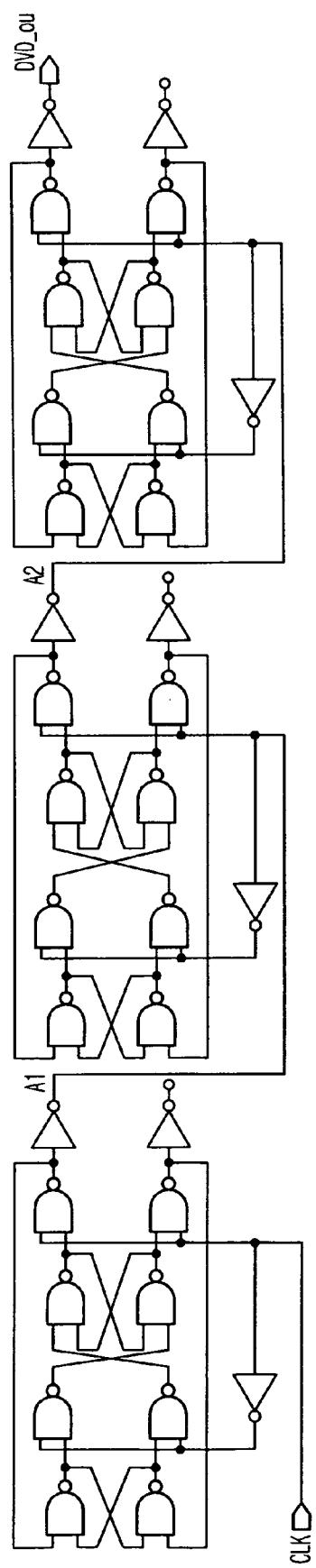
FIG. 3 describes a detailed circuit diagram of a clock divider unit in the prior art.
Figure 4:
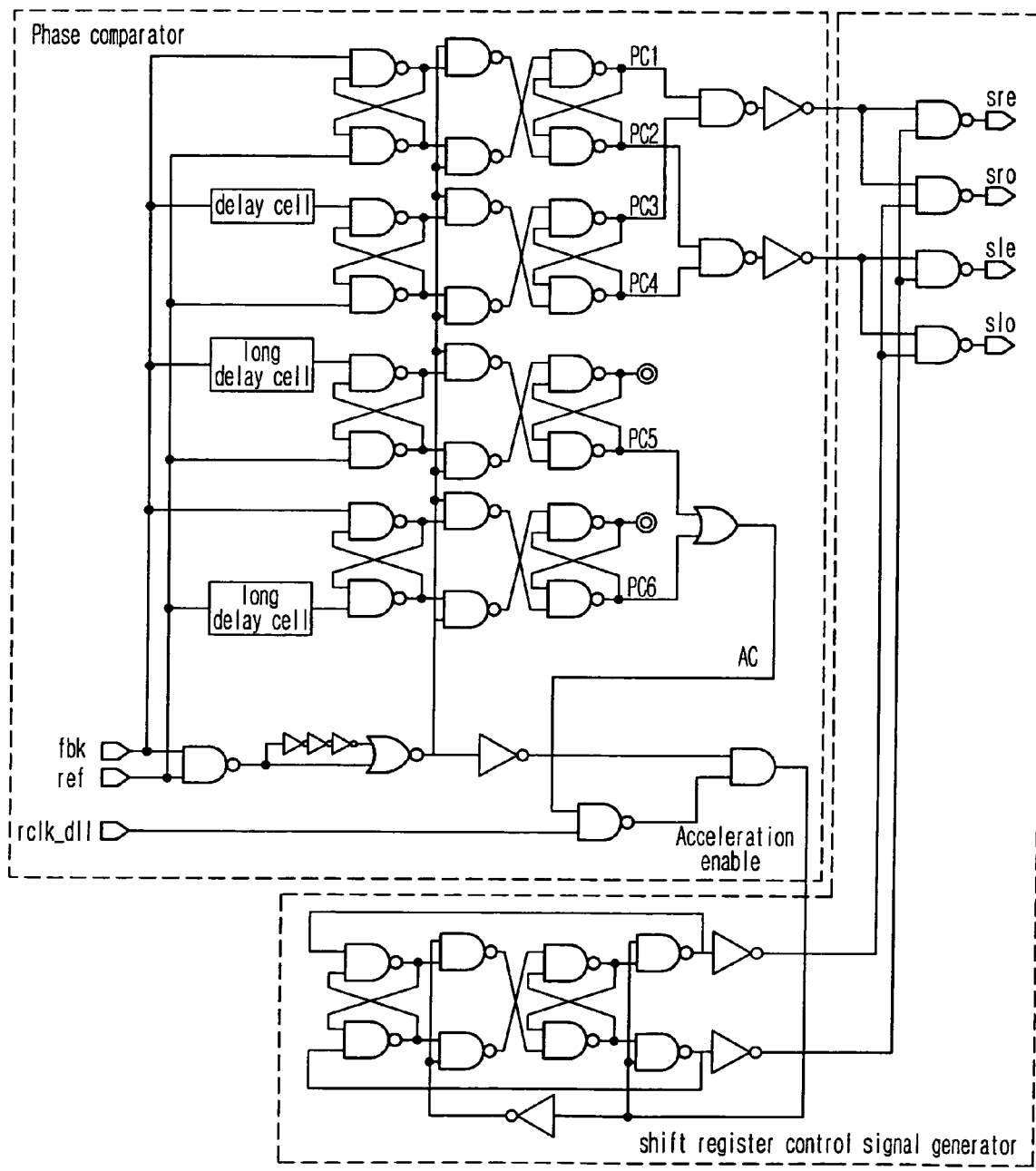
FIG. 4 shows a detailed circuit diagram of a phase comparator unit in the prior art.
Figure 5:
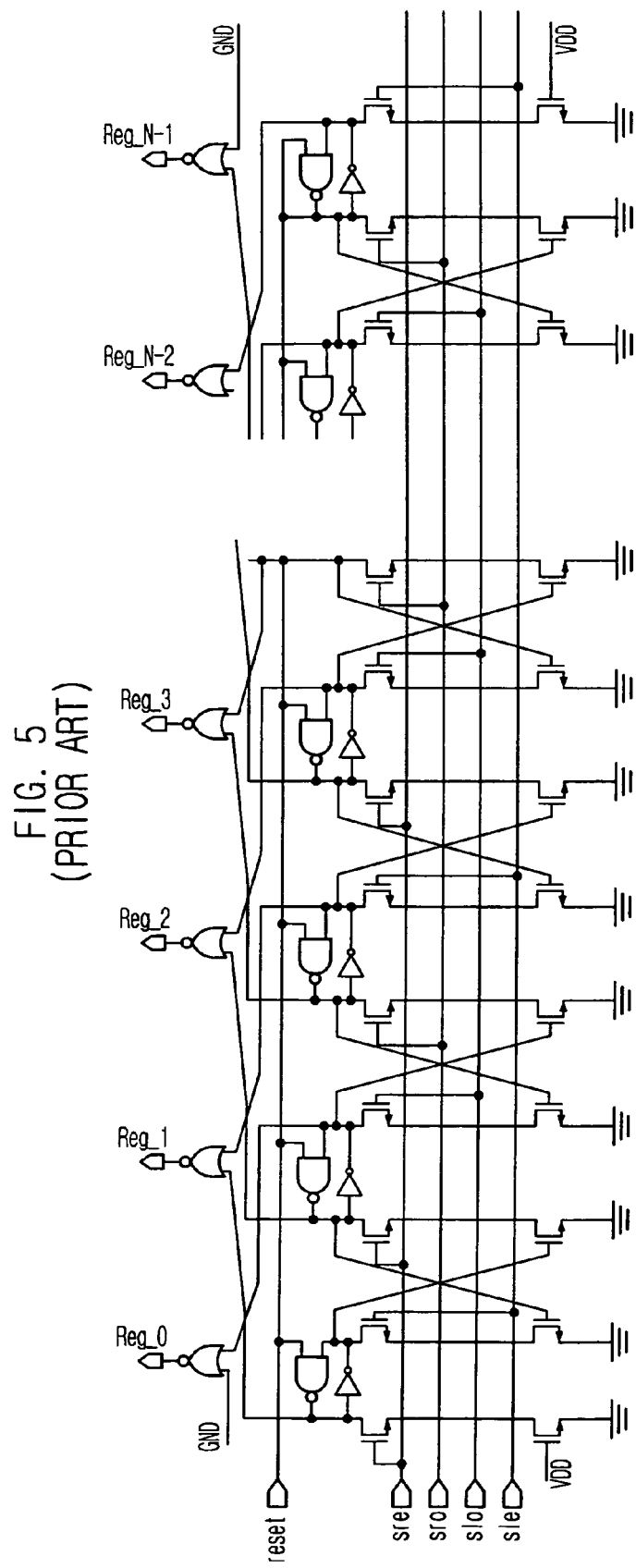
FIG. 5 represents a detailed circuit diagram of a delay control unit in the prior art.
Figure 6:
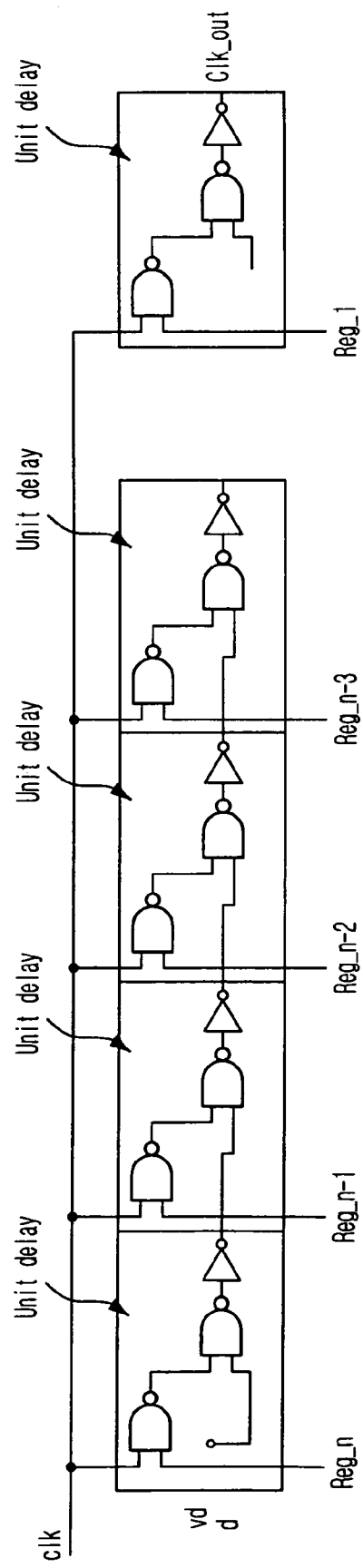
FIG. 6 illustrates a detailed circuit diagram of a delay line unit in the prior art.
Figure 7:
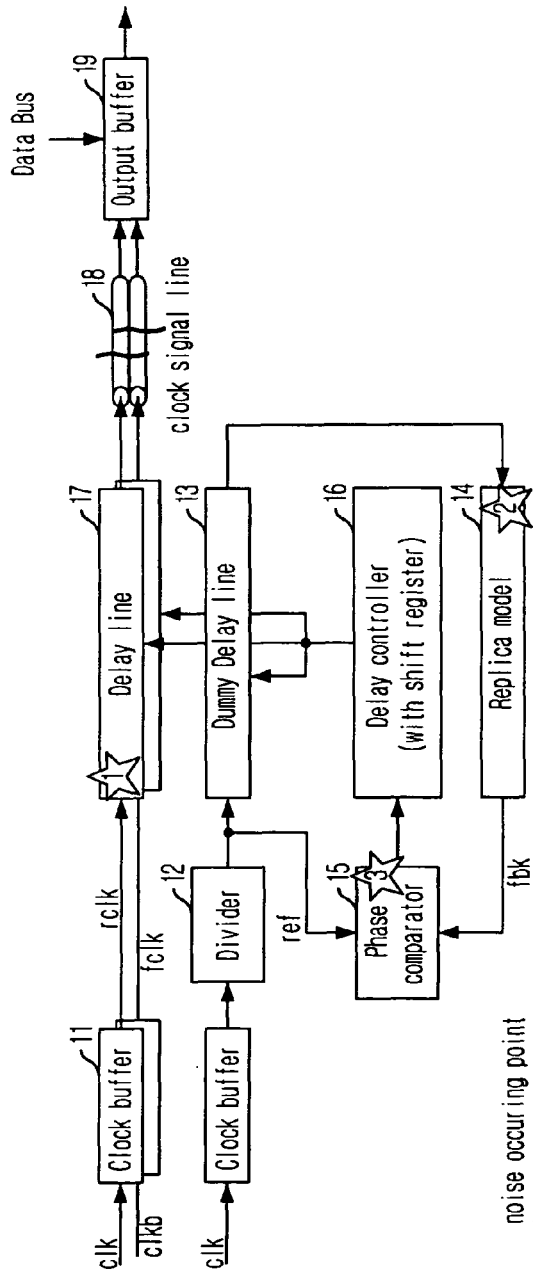
FIG. 7 shows a diagram for exemplifying case by case a reaction time and applying time of noise that occurs in a DDL circuit in the prior art.
Figure 7:
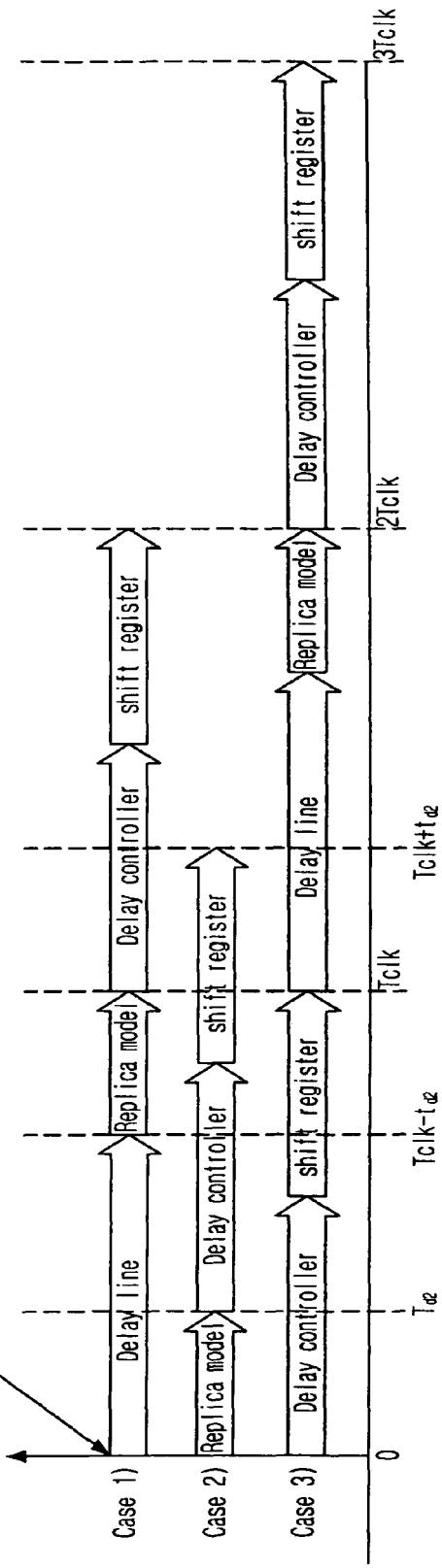
Figure 8:
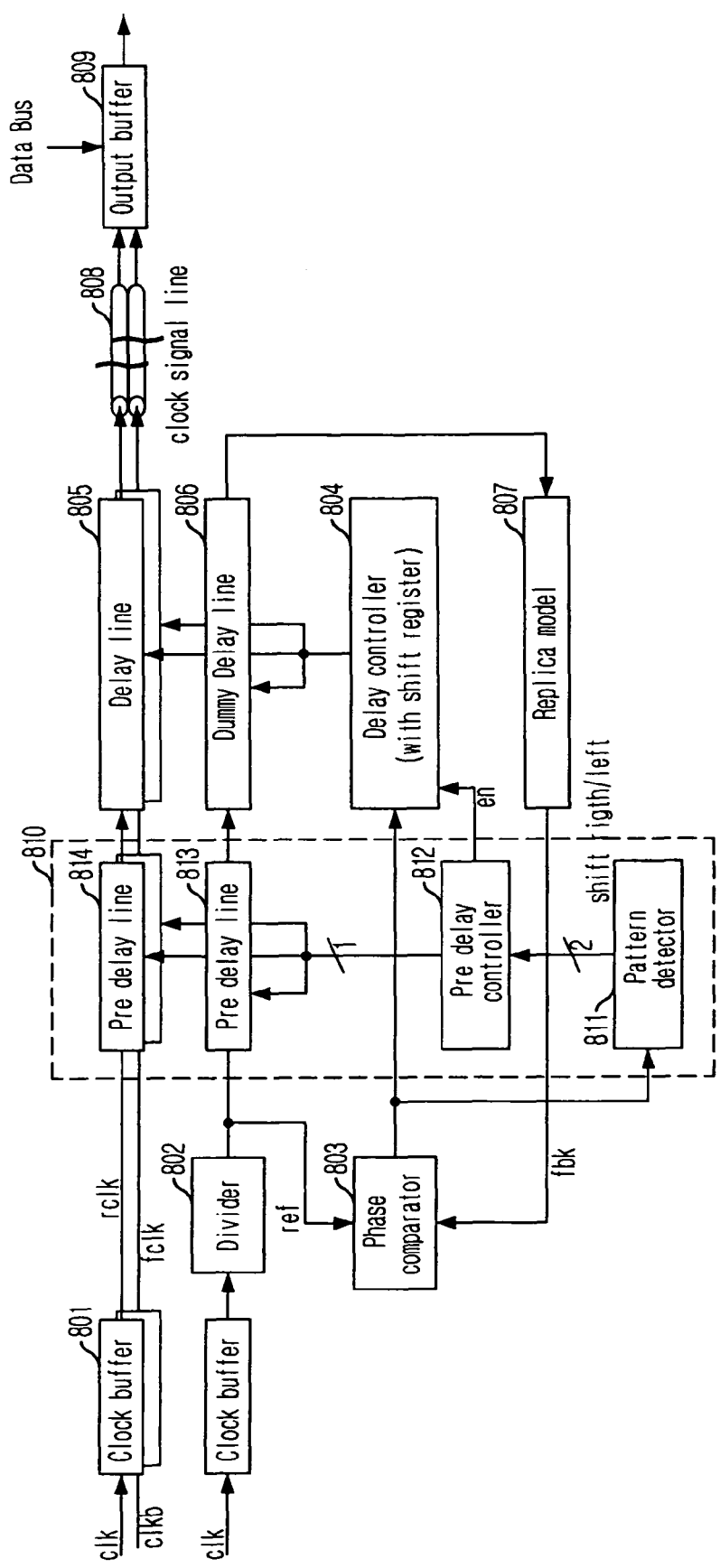
FIG. 8 provides a DLL in accordance with the present invention.

FIG. 8 provides a DLL (Delay Locked Loop) in accordance with the present invention.

The DLL according to one embodiment of the present invention comprises a pitch out unit added to a conventional DLL. Particularly, the pitch out unit 810 includes, not limited to, pre-delay lines 813, 814 that are positioned in front of delay lines 805 for a rising internal clock rclk and a falling internal clock fclk and in front of a dummy delay line 806, respectively, a pattern detector 811 for detecting and storing a generated noise pattern, and a pre-delay controller 812 for controlling the delay amount of the pre-delay lines 813, 814 depending on the output of the pattern detector 812.

Generally, the DLL goes to the locked state after a while from its initial operation. After that, various commands are inputted into the DRAM and a jitter due to external or internal noise would happen in the DLL. At that time, the pitch out unit 810 monitors result from a phase comparator depending on the respective command and collects noise pattern data. Once the collected noise pattern data reach a predetermined amount, the pattern generator receives the noise pattern data to calculate the average value. Here, the predetermined amount may be the data amount when a counter in a second storage cell manager 902-2 is fully counted according to one embodiment of the present invention. On the other hand, after the average value is calculated, those data may be stored at first storage blocks 907-1, . . . , 907-N that are managed by the first storage cell manager 902-1. After that, when a new command is inputted, the stored value is transferred to the pre-delay controller 812. It will be desirable to control to stop the operation of the delay controller 804 while the pre-delay controller 812 is operating.

Figure 9:
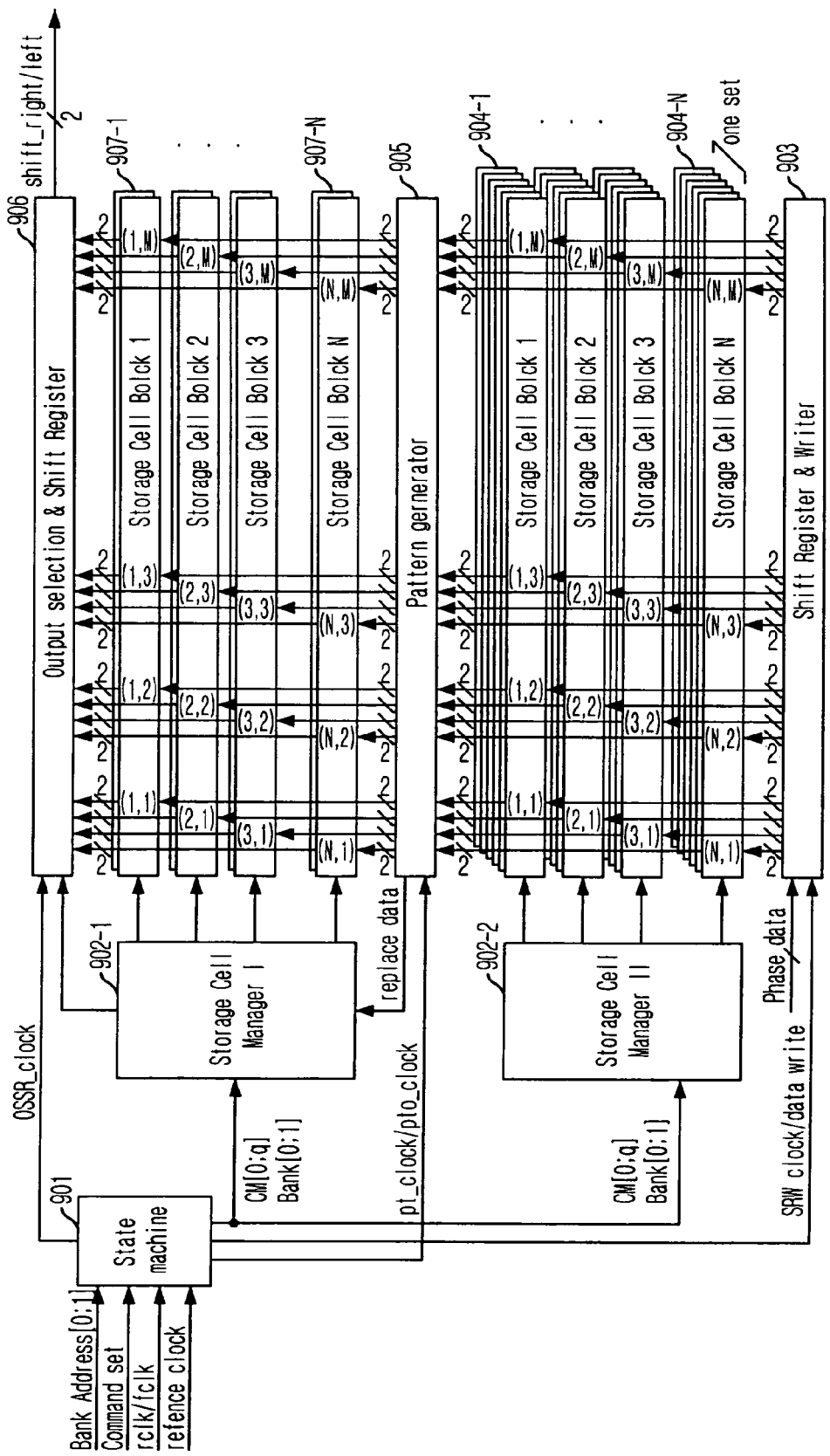
FIG. 9 offers a block diagram of a pattern detector in accordance with one embodiment of the present invention.

FIG. 9 offers a block diagram of the pattern detector 811 in accordance with one embodiment of the present invention.

The pattern detector 811 according to one embodiment of the present invention includes a state machine 901 for controlling the first and the second storage cell managers 902-1, 902-2, first and second storage blocks 904-1, . . . 904-N, 907-1, . . . , 907-N for storing the result of the phase comparator 803, the first and the second storage cell managers 902-1, 902-2 for reading and writing data from/to the first storage blocks 907-1, . . . , 907-N and the second storage blocks 904-1, . . . , 904-N, a shift register and writer 903 for performing shift operation and up-loading data by using the result of the phase comparator 803, a pattern generator for generating a pattern of noise data based on the collected data, and an output selecting and shift register 906 for transferring the stored noise pattern data to the pre-delay controller 812.

For example, it will be described for the operation of the pattern detector 811.

When a read command for bank 0 is inputted from outside, e.g., from a chipset to the state machine 901, the inputted read command is decoded at the state machine 901 that outputs a signal corresponding to the bank 0 and the read command to the first and the second storage cell managers 902-1, 902-2. According to one embodiment, by making one of CM[0;q] outputs corresponding to the read command be in "H" state, the bank 0 gets in the 'H' state and the bank 1-3 get in 'L' state. The first and the second storage cell managers 902-1, 902-2 that received the above signal selects one storage cell block of the first and the second storage blocks, respectively. Then, the second storage blocks 904-1, . . . , 904-N receives and stores the noise data from the shift register and writer 903 when the shift register and writer 903 is full of the result of the phase comparator 903.

As one example, when the storage cell block 904-3 of the second storage blocks 904-1, . . . , 904-N is selected by the second storage cell manager 902-2, data from the shift register and writer 903 are stored in the addresses that are not occupied by any data in the storage cell block 904-3 in order by an internal counter of the second storage cell manager. If the first address 904-3-1 to the k-th address 904-3-$k$ in the storage cell block 904-3 are full of data, data is stored after the address that is counted by the counter. Here, as the storage cell block 904-3, each of the second storage blocks have k data addresses, each address having two storage cells, to have 2×k storage cells. At this point, the reason why each address needs two storage cells is that 2 bits are needed for one data to store −1, 0, 1 values.

Also, when the storage cell block 904-3 is full of data, the state machine 901 sends a signal, that notices that the storage cell block 904-3 is full of data, to the pattern generator 905. The pattern generator 905 uses the data that are stored at the storage cell block 904-3 to generate the noise pattern. If the storage cell block 904-3 is not full of data, the pattern generator 905 does not perform any operation. The noise pattern data that is generated by the pattern generator 905 is stored at the storage cell block 907-3 under control of the first storage cell manager 902-1.

If the storage cell block 907-3 that is controlled by the first storage cell manager 902-1 have stored the noise pattern data already, the noise pattern data is loaded by the output selecting and shift register 906 to control the pre-delay controller 812.

In other words, the pattern detector 811 performs 3 major functions as follows.

DLL noise data collection,
DLL noise pattern generation, and
DLL noise pattern reload as the same condition.
It will be described for the above functions in detail.
DLL noise data collection function:

When noise is inputted to or occurs in the DLL, the phase comparator outputs a control signal to change the delay line due to the noise, by which noise input or occurrence can be determined. The major roll of this function is to collect the result of the phase comparator in the storage cells. On the other hand, the data is collected, for example, under the rule as follows. One of the major portions of the current that is consumed in the DRAM is that for reading or writing data in the DRAM cell array. Of course, when reading or writing, noise varies depending on the location of the accessed bank in the DRAM cell array and successive inputs of the read commands. By classifying these factors, data can be grouped by operations having correlation. That is, not limited to, after grouped by the command roughly, data is grouped between the commands depending on the accessed address (bank) in detail. By classifying as such, the noise pattern data can be classified up to M times.

DLL noise pattern generation function:

Upon collecting a predetermined amount of data with performing the DLL noise data collection function, the average of the collected data is calculated to have a representative value. The procedure for determining the representative is as follows.

First, all the data that belong to a same classified group among the stored data in the second storage blocks 904-1, . . . , 904-N are added to a sum. Then, based on the summed value, the representative value is obtained by performing a threshold operation depending on the total data set (data set that belongs to the same group). For example, when one set has 5 data storage cells, let's assume that the results of the phase comparator are collected at each of the storage cell blocks as following Table 1.

TABLE 1

|      |   | Seq1 | Seq2 | Seq3 | Seq4 | Seq5 | Seq6 | Seq7 | Seq8 |
|------|---|------|------|------|------|------|------|------|------|
| Unit | 1 | 0    | 1    | −1   | 0    | −1   | 1    | 1    | 0    |
| Set  | 2 | 0    | 1    | 0    | −1   | −1   | 1    | 1    | 0    |
|      | 3 | 1    | 0    | 0    | −1   | −1   | 0    | 1    | 1    |
|      | 4 | 0    | 1    | 0    | −1   | 0    | −1   | 1    | 1    |
|      | 5 | 1    | 0    | 0    | 0    | −1   | 1    | 0    | 1    |
| SUM  |   | 2    | 3    | −1   | −3   | −4   | 2    | 4    | 3    |
| AVERAGE | | 0  | 1    | 0    | −1   | −1   | 0    | 1    | 1    |

As shown in Table 1, 5 collected results are summed. Here, letting '1' mean shift right, '−1' mean shift left, and '0' mean holding, the collected values are added to have a sum. After dividing the added value by 5, the representative value for each set can be obtained to be 0 when the absolute value of the summed value is less than 2.5, 1 when the summed value is greater than +2.5, and −1 when the summed value is less than −0.5.

DLL noise pattern reload at the same condition function:

The noise pattern data that is generated by performing the DLL noise pattern generation function is loaded under the same condition, i.e., the same command and the bank access. Particularly, under the same condition, the noise pattern data controls the pre-delay controller 812 as the phase comparator 804. At this point, the data that are compared at the phase comparator 804 may be neglected while the pre-delay controller 812 is driven. Also, because the early-collected noise pattern data is out-of-date data by 1 to 3 cycles at that point of noise generation, data can be applied after neglecting the 2-cycle-earlier data from the command. That is, in the example shown in Table 1, the average that is inputted to the pre-delay controller should be 0 −1 −1 0 1 1 after input of the command.

Figure 10:
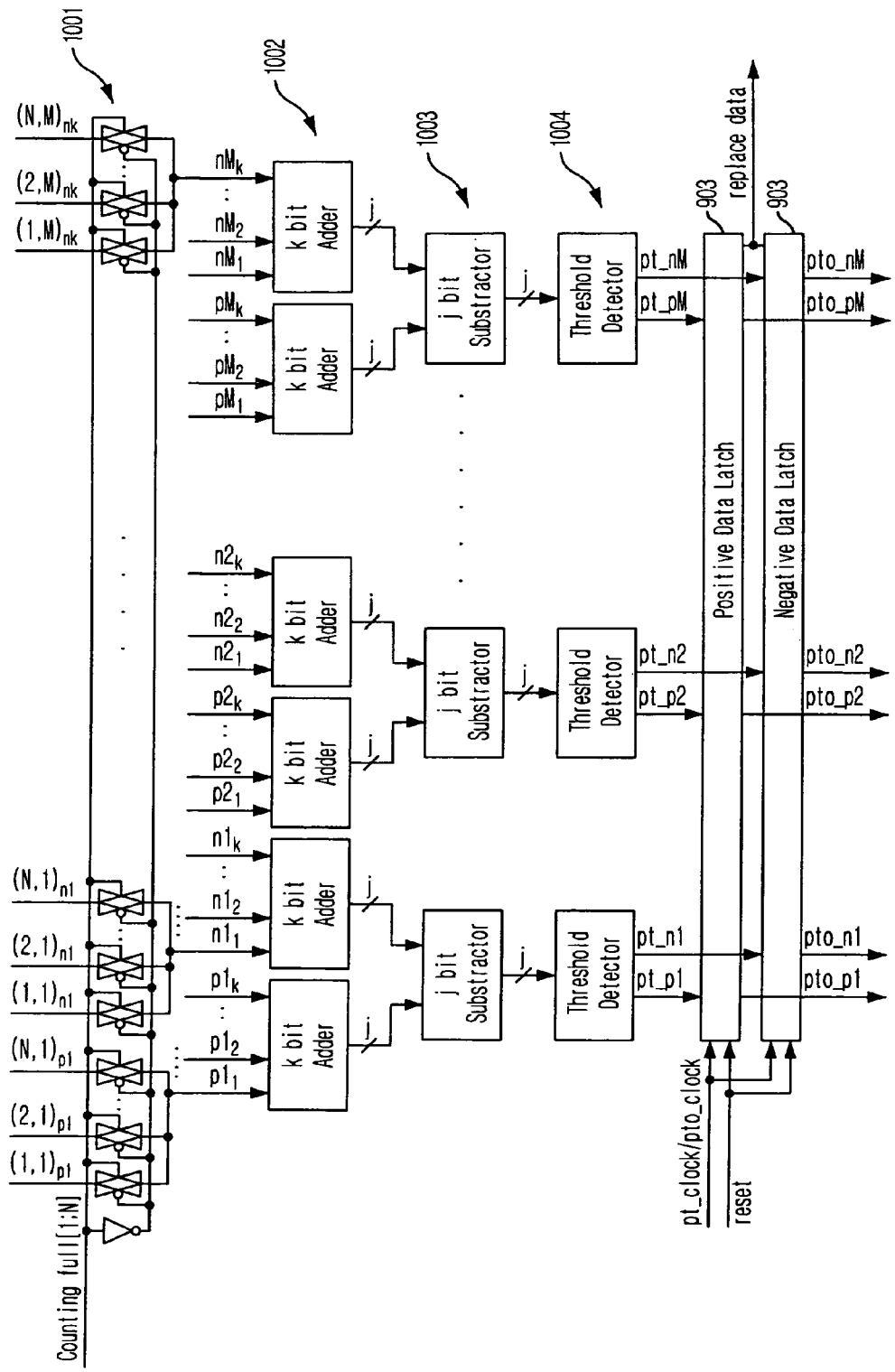
FIG. 10 presents a block diagram of a pattern generator in accordance with one embodiment of the present invention.

FIG. 10 presents a block diagram of the pattern generator in accordance with one embodiment of the present invention.

When one of the storage cell blocks is full according to the counter of the second storage cell manager 902-2 to output the most significant bit of the counter (e.g., when the 2-bit counter outputs 1 1 mod 2), a transfer gate 1001 that is coupled to the storage cell block full of the data in the pattern generator 905 is opened. On the other hand, N counting full signals that are inputted to the transfer gate 1001 in the pattern generator 905 are the output signals that are outputted from the N counters that control the N storage cell blocks 904-1, . . . , 904-N in the second storage block. Here, the storage cell block 904-1 stores the noise data that is generated by the bank 0 and the command 1. The storage cell block 904-2 stores the noise data that is generated by the bank 0 and the command 2. Each of the storage cell blocks stores the noise data similarly and the storage cell block 904-N stores the noise data that is generated by the bank 3 and the command Q.

When the transfer gate 1001 is opened, the data is inputted to the second storage block 904 and the inputted data are to have one of 3 states after going through the processing circuits for patterning the noise data. That is, if the added and subtracted value of the noise pattern data has a positive value greater than a threshold, the state gets 1, if an integer less than a threshold, the pattern data takes 0, and if a negative value less than a threshold, it takes −1.

The pattern generator 905 takes the average value after adding the k data that are stored at an individual storage cell block, e.g., the storage cell block 904-3. Still, for the data of −1, as described above, because the phase shift data are outputted through 2 or more pins in the phase comparator 803, 2 k-bit adders 1002 can be used. When the phase shift right is +1, the phase shift left may be −1. The respective values are added and then subtracting at a j-bit subtractor 1003. Based on that result, 0 is obtained when the value after a threshold detector 1004 is less than a predetermined value and 1 is obtained when greater than a predetermined value. The signal that went through the threshold detector 1004 goes into the data latches 1005-1, 1005-2 and then is stored at the first storage blocks 907-1, . . . , 907-N.

The transfer gate 1001 of the pattern generator 905 receives the counting full signal counting full_[1;N] to connect the path for the input data. The connected data path are the shift right/left (noted as positive/negative) (p/n) of the phase comparator, respectively. The inputted data go through the adder 1002, the subtractor 1003 and the threshold detector 1004 and temporally stored at the latches 1005-1, 1005-2 until a signal pro_clock is inputted, and then put into the first storage blocks 907-1, . . . , 907-N that are managed by the first storage cell manager 902-1.

Figure 11:
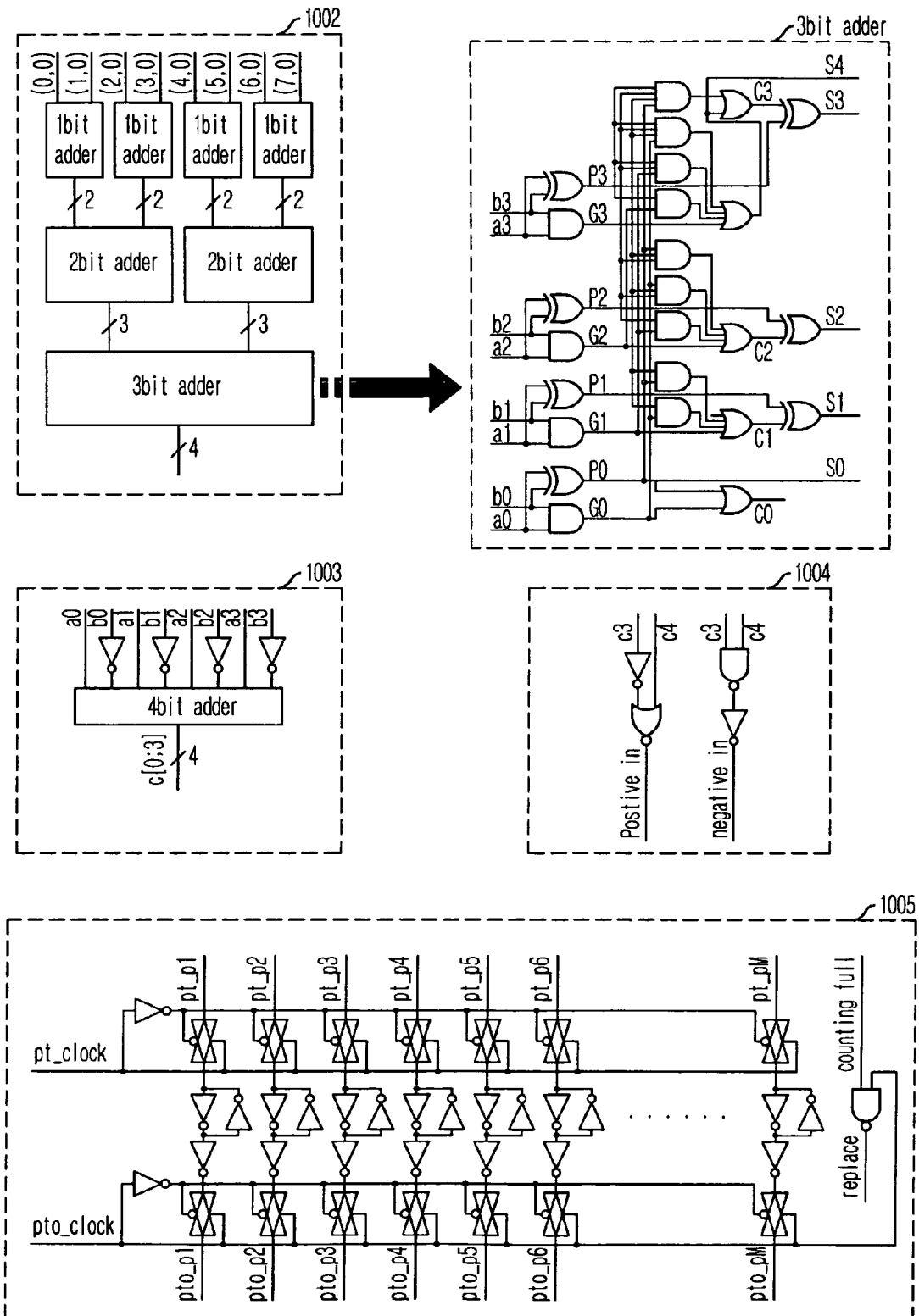
FIG. 11 shows a detailed circuit diagram of a pattern generator in accordance with one embodiment of the present invention.

FIG. 11 shows a detailed circuit diagram of the pattern generator in accordance with one embodiment of the present invention.

According to one embodiment of the present invention, the adder 1002 of the pattern generator 905 adds 8-bit data. At this point, each of the 8-bit shift right data and the shift left data are inputted to the adder 1002, respectively. On the other hand, the inputs to the data latches 1005-1, 1005-2 of the pattern generator 905 are controlled by a signal pt_clock that uses the rising clock rclk of the DLL, and the outputs from the data latches 1005-1, 1005-2 are controlled by a signal pto_clock that uses the falling clock fclk of the DLL. Accordingly, the phase of the pt_clock signal is different from that of the pto_clock signal by 180 degrees.

Further, when the data are stored at the data latches 1005-1, 1005-2, the data latch 1005-1 outputs a replace signal to the first storage block 907. The replace signal that is generated by logically combining the counting full signal and the pto_clock operates the first storage cell manager 902-1 to store the data in the desired storage cell block in the first storage block 907.

Figure 12:
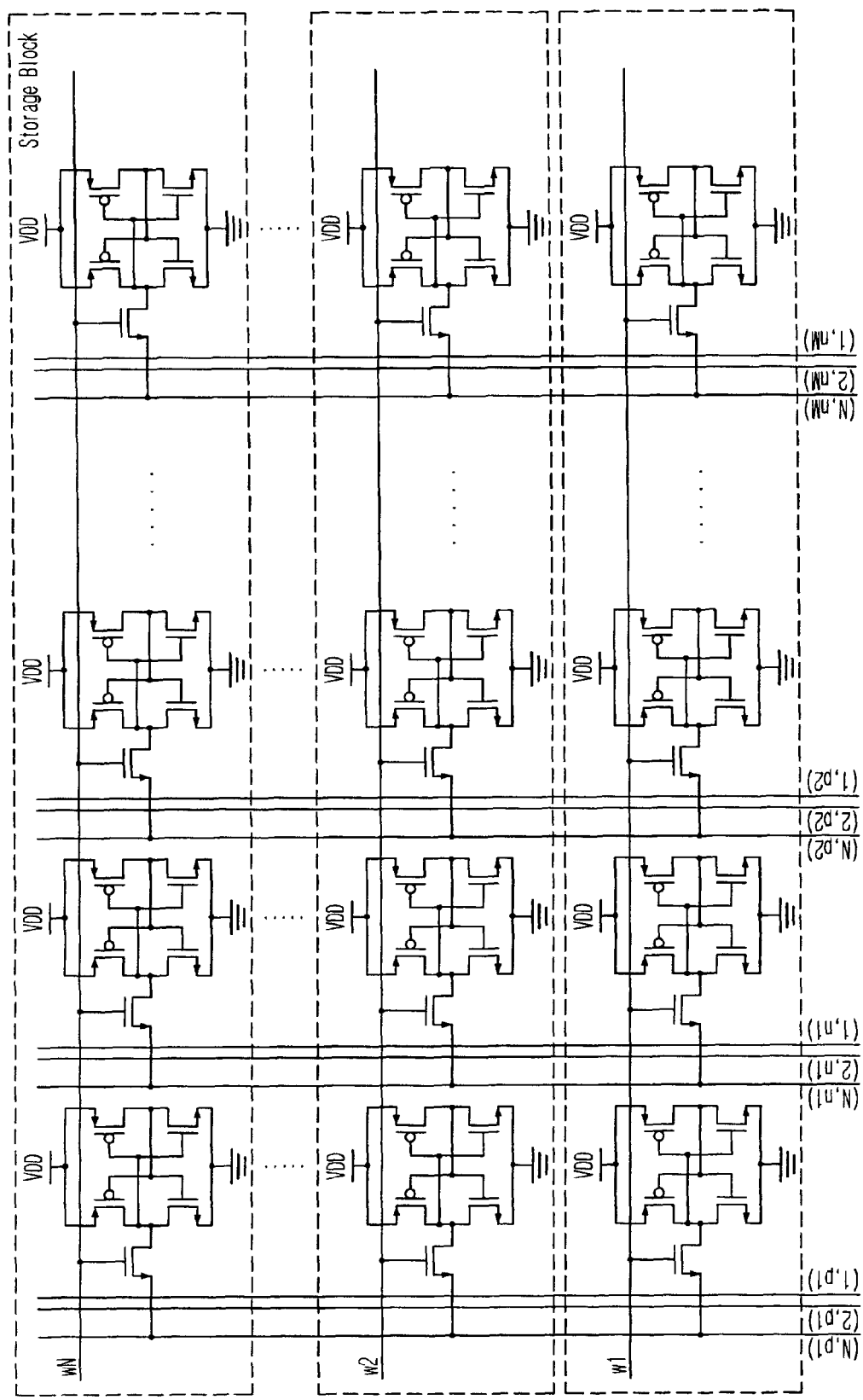
FIG. 12 represents a detailed circuit diagram of a storage cell block in a pattern generator in accordance with one embodiment of the present invention.

FIG. 12 represents a detailed circuit diagram of the storage cell block in the pattern generator in accordance with one embodiment of the present invention.

The storage cell in the storage cell block may be constructed with using CMOS latch circuits, and an NMOS transistor acts as a switch to read or write the data. The storage cell block may store the shift right data and the shift left data.

Figure 13:
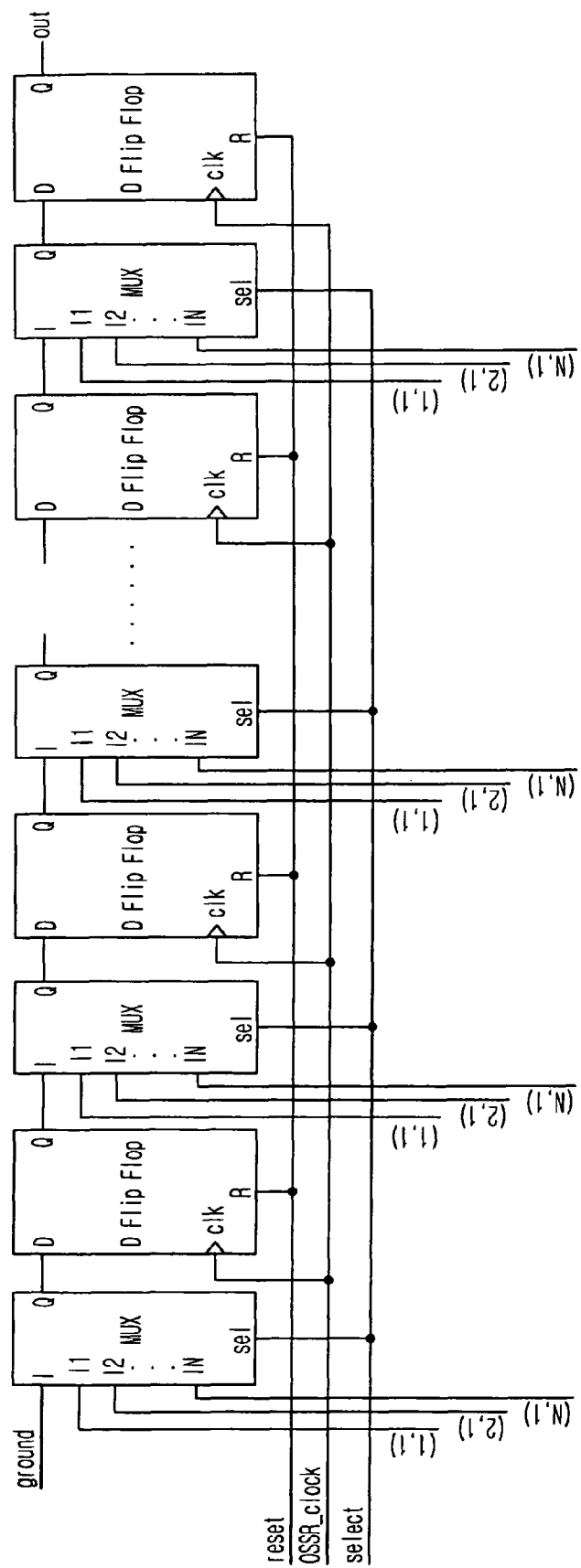
FIG. 13 illustrates a circuit diagram of an output selecting and shift register in accordance with one embodiment of the present invention.

FIG. 13 illustrates a circuit diagram of the output selecting and shift register in accordance with one embodiment of the present invention.

The output selecting and shift register may be constructed with a plurality sets of a multiplexer and a D-F/F (flipflop), the sets being serially coupled to each other. The output selecting and shift register transfers the stored noise pattern data to the pre-delay controller. The output selecting and shift register selects one of the connected storage cell blocks based on information from the state machine to receive the data, and then performs shift operation to provide information to the pre-delay controller. Here, the rising clock rclk that is inputted to the DLL may be used as the clock OSSR_clock. On other hand, the output of each storage cell block is inputted the corresponding multiplexer under control of the select signal from the decoder in the storage cell manager.

Figure 14:
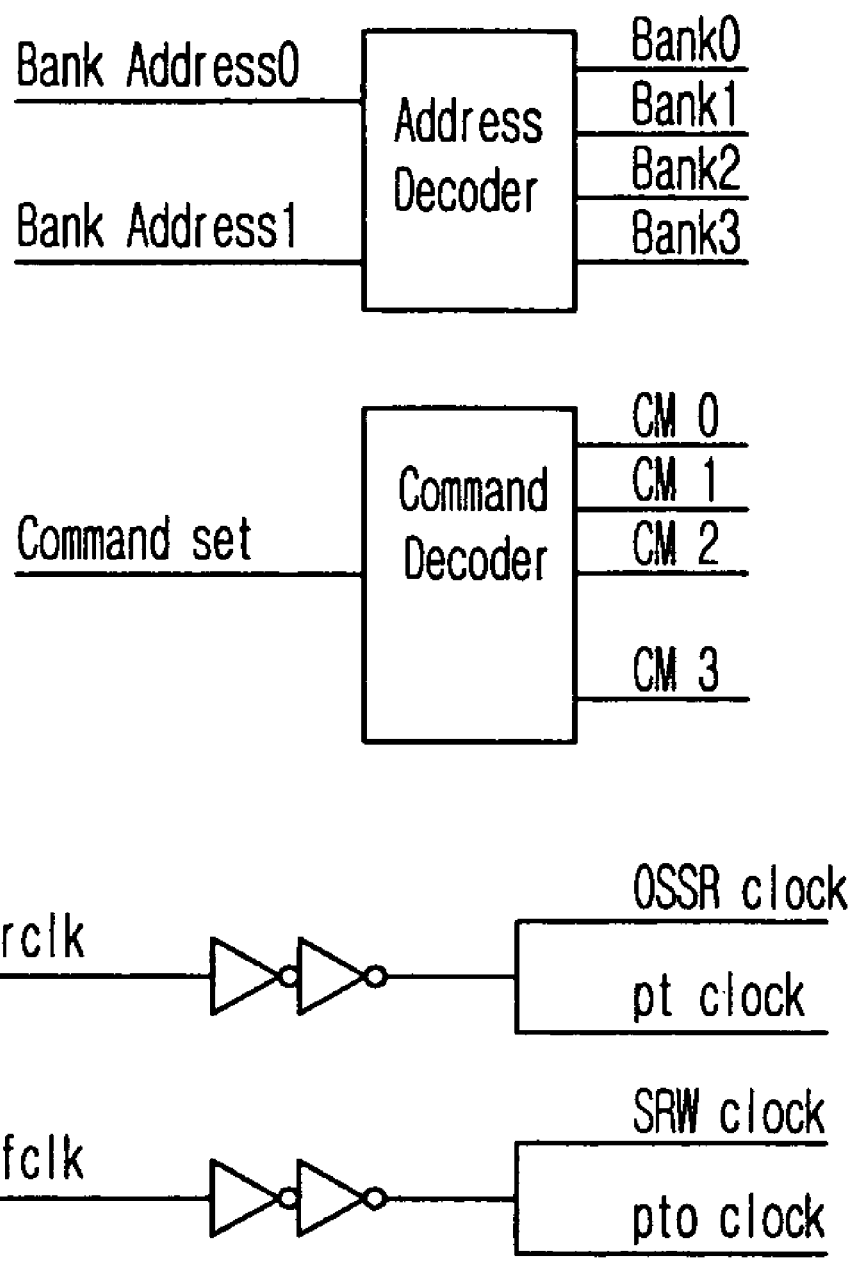
FIG. 14 provides a circuit diagram of a state machine in accordance with one embodiment of the present invention.

FIG. 14 provides a circuit diagram of the state machine in accordance with one embodiment of the present invention.

The state machine controls the first and the second storage cell managers that manage the storage cell blocks. By using the externally inputted command, bank, address and clock, it controls to classify the data by the command and by the accessed bank to store the data at the second storage block, and controls to read the classified data by the command and by the accessed bank. For example, when a command for reading the bank 0 in the DRAM is inputted to the DRAM from an external chipset, a predetermined logic signal is inputted to the input bank address 0/1 of the address decoder to output the 'H' state only through the bank 0 of the outputs of the address decoder and the 'L' state through the rest banks 1-3 of the address decoder. Further, CAS='L' and RAS='H' corresponding to the read command are inputted to the command set, the input of the command decoder, to output the "H" state only through the CM output that is assigned to the read command and the 'L' state through the rest outputs.

Figure 15:
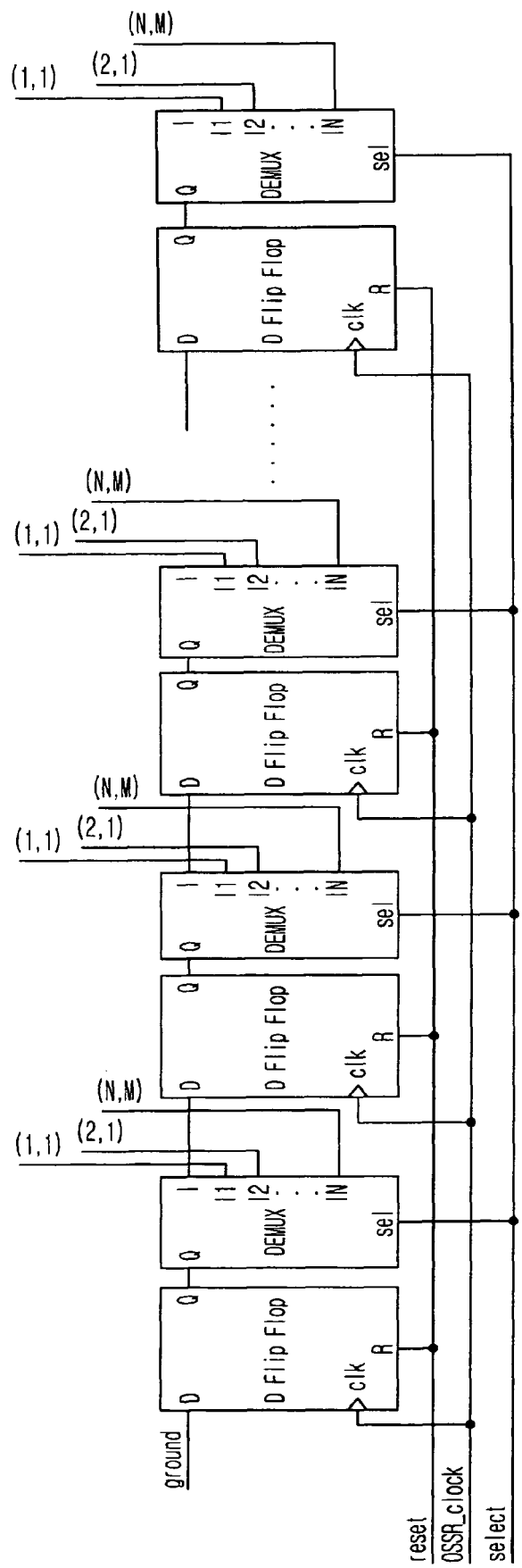
FIG. 15 offers a circuit diagram of a shift register and writer in accordance with one embodiment of the present invention.

FIG. 15 offers a circuit diagram of the shift register and writer in accordance with one embodiment of the present invention.

The shift register and the writer may be constructed by a plurality of sets of a demultiplexer and a D-F/F, each set being serially coupled to each other. The shift register and writer receives the results of the phase comparator to perform the shift operation and fills the register with the data, and then up-loads the data to the storage cell block. The demultiplexer can be operated by receiving the address of the storage block which will be used by the state machine as same as the output selecting and shift register in FIG. 13. Still, the storage cell block that will be used is the storage cell block that supplies the data to the noise pattern generator. The clock SRW_clock that is used in the shift register and writer may use the falling clock fclk of the DLL. The select signal for controlling the demultiplexer may use the output of the decoder of the first storage cell manager.

Figure 16:
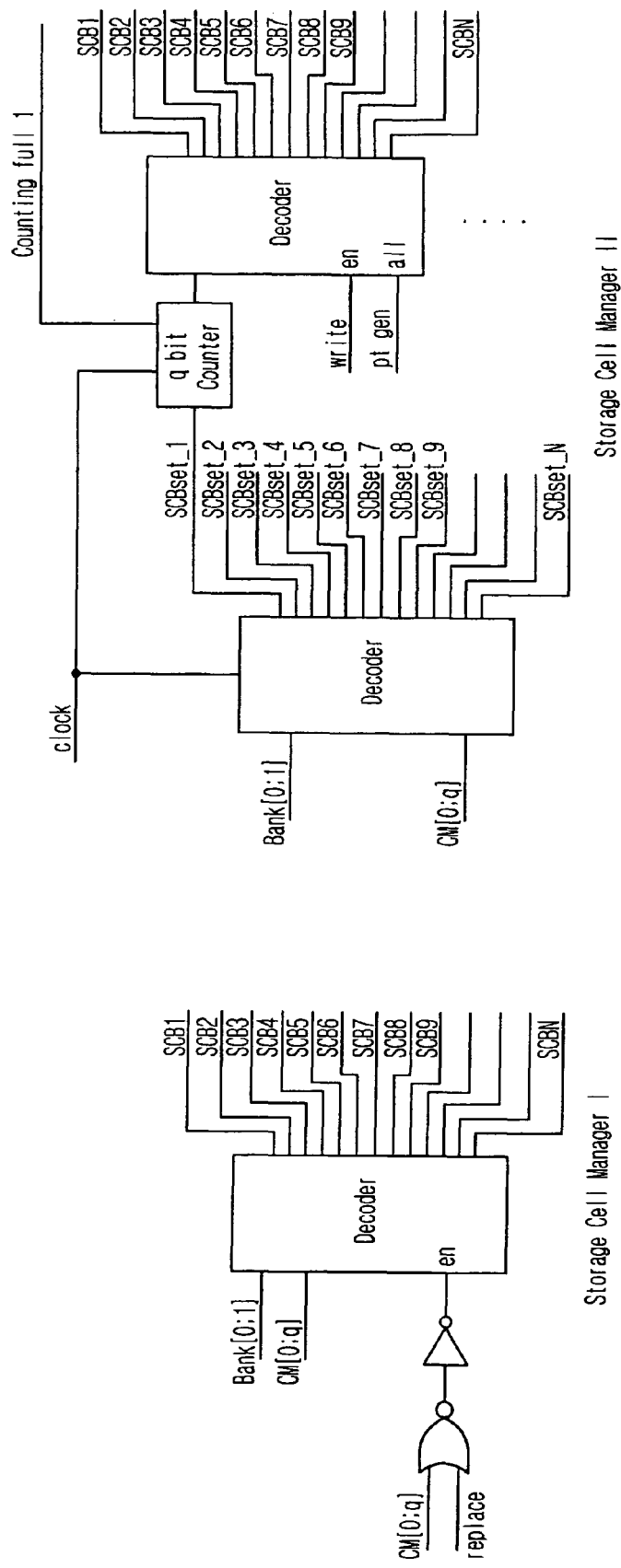
FIG. 16 is a circuit diagram of a storage cell manager in accordance with one embodiment of the present invention.

FIG. 16 is a circuit diagram of the storage cell manager in accordance with one embodiment of the present invention.

The first storage cell manager 902-1 manages the first storage block 907 to select a desired storage cell block of the first storage block to write or read the data. The first storage cell manager includes the decoder for selecting the storage cell block that will be read from or written to. The decoder is enabled when a command is inputted or the replace signal on the 'H' state is inputted. When the decoder is disabled, all its outputs take the 'L' state.

The second storage cell manager 902-2 manages the second storage block 904 for storing the noise data and its operation is very similar to that of the first storage cell manager 902-1 except that the second storage cell manager 902-2 stores the noise having same condition with one set of several blocks during read operation or write operation so as to request 2 decoders. The first decoder, for example, selects one storage cell block 904-3 of the plurality of storage cell blocks 904-1, . . . , 904-N in the second storage block 904. The second decoder selects one of the addresses in the selected storage cell block 904-3. Further, data storage order within the each storage cell block may be assigned by using the counter. Each of the storage cell blocks is a data group for a same command and a same access bank. If information that will be inputted into one of the storage cell blocks is fully collected by using the counter, the data can be transferred to the pattern generator 905.

Figure 17:
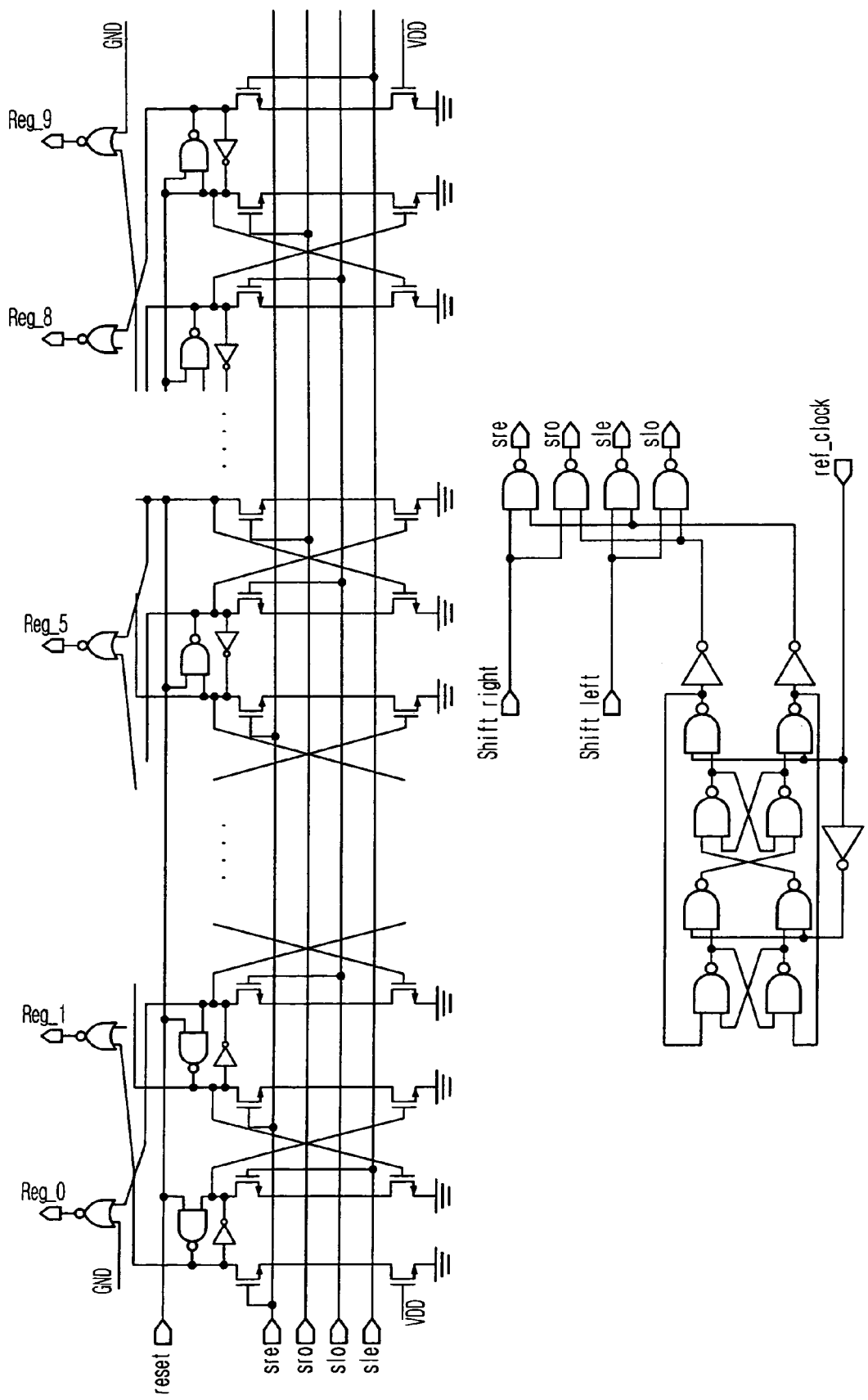
FIG. 17 represents a circuit diagram of a pre-delay controller in accordance with one embodiment of the present invention.

FIG. 17 represents a circuit diagram of the pre-delay controller 812 in accordance with one embodiment of the present invention.

The pre-delay controller 812 that is constructed similarly as the delay controller 804 is controlled not by information that is feedback from the phase comparator but by feedback control from the pattern detector 811. That is, the pre-delay controller 812 performs shift left or shift right on the delays of the pre-delay lines 813, 184 in response to the output of the pattern detector 811 so as to vary the amount of the delay. For example, when the output selecting and shift register of the pattern detector 811 outputs the shift right signal of the 'H' state, a shift right even signal sre and a shift right odd signal sro are continuously outputted in addition to a pulse that is generated by a reference clock ref_clock in a T-F/F to perform shift right on the delays of the pre-delay lines 813, 184.

Figure 18:
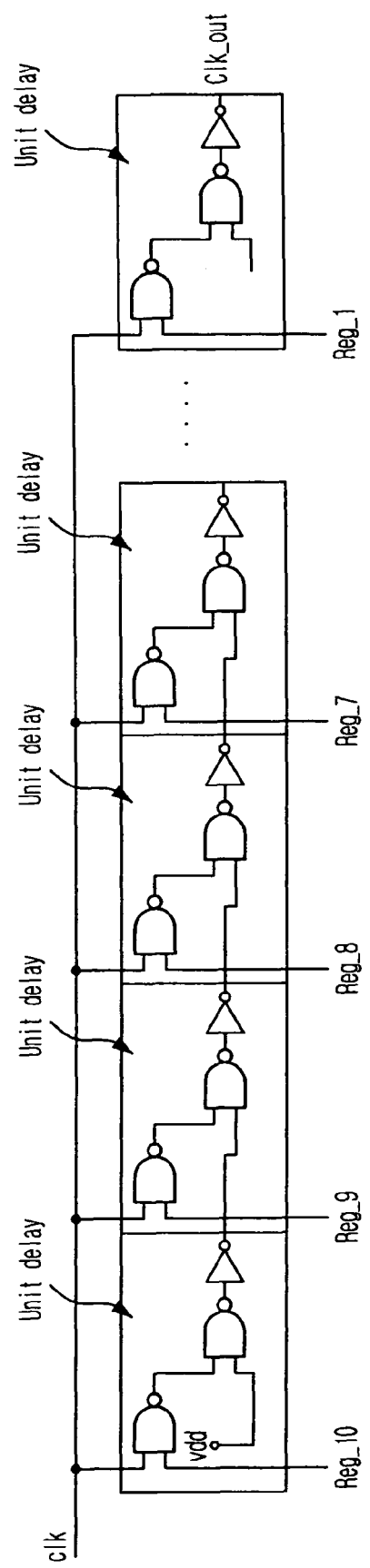
FIG. 18 offers a circuit diagram of a pre-delay line in accordance with one embodiment of the present invention.

FIG. 18 offers a circuit diagram of the pre-delay line in accordance with one embodiment of the present invention.

The number of the unit delay cells in each of the pre-delay lines that are located before the delay lines and the dummy delay line are equal to or less than the number of the unit delay cells of each delay line. That is, it is enough to have the unit delay cells in each of the pre-delay lines for coping with the noise and some extras. According to one embodiment of the present invention, the pre-delay line may be constructed with 10 unit delay cells.

As described above, according to the present invention, the jitter component that inevitably occurs due to feedback latency in the conventional DLL can be removed. That is, the present invention has benefit of removing the jitter component by controlling the delay lines based on the predicted data.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A delay locked loop, comprising:
    a phase comparator configured to compare a phase of a reference clock signal with a phase of a feedback clock signal;
    a delay line configured to delay an internal clock based on a comparison result from the phase comparator to output the feedback clock signal; and
    a pitch out unit configured to monitor the comparison results depending on commands inputted to the delay locked loop to generate and store noise patterns by detecting noise data corresponding to the commands and to determine a delay amount of the delay line based on stored noise patterns when the commands are inputted.

2. The delay locked loop as recited in claim 1, wherein the pitch out unit includes:
    a pattern detecting unit configured to generating and storing the noise pattern based on the comparison result; and
    a delay control unit configured to determine the delay amount of the delay line depending on the output of the pattern detecting unit.

3. The delay locked loop as recited in claim 2, wherein the pattern detecting unit includes:
    a storage block configured to store noise data and the noise pattern;
    a storage cell manager configured to read or write the noise data and the noise pattern of the storage block under control of a state machine;

a shift register and writer configured to perform shift operation by using the comparison result and up-load the noise data; and a pattern generator for generating the noise pattern based on the noise data.

4. The delay locked loop as recited in claim 3, wherein the storage block includes:

a first storage block for storing the comparison result; and a second storage block for storing the noise pattern.

5. The delay locked loop as recited in claim 4, wherein the storage cell manager includes:

a first storage cell manager for writing inputted data or reading stored data by selecting a desired storage cell block in the first storage block; and a second storage cell manager for writing inputted data or reading stored data by selecting a desired storage cell block in the second storage block.

6. The delay locked loop as recited in claim 5, wherein the second storage cell manager includes:

a first decoder for selecting one of a plurality of the storage cell blocks in the second storing block; and a second decoder for selecting one of a plurality of addresses in the selected storage cell block.

7. The delay locked loop as recited in claim 6, wherein the second storage cell manager further includes a counter for assigning data storing order in the selected storage cell block.

8. The delay locked loop as recited in claim 7, wherein the selected storage cell block stores data having a same command and a same access bank.

9. The delay locked loop as recited in claim 3, wherein the pattern generator includes:

a plurality of adders for adding an inputted data;

a plurality of subtractors for subtracting the output of the adders;

a plurality of threshold detectors for performing threshold operations for the outputs of the subtractors; and a plurality of data latches for temporally storing the noise pattern that is outputted from the threshold detectors.

10. The delay locked loop as recited in claim 3, wherein the state machine controls data to be stored in the storage block by classifying the data by command and by accessed bank by using a command, a bank address and a clock, that are externally inputted, and controls to read the data that is stored at the storage block by classifying by command and by accessed bank.

* * * * *